(12) United States Patent
McCullough

(10) Patent No.: US 11,246,536 B2
(45) Date of Patent: Feb. 15, 2022

(54) GASTROENTEROLOGICAL DIAGNOSTIC TEST FOR THE DETERMINATION OF PH IN THE DIGESTIVE TRACT FOR ASSESSMENT OF DYSFUNCTION

(71) Applicant: Tim McCullough, Friendswood, TX (US)

(72) Inventor: Tim McCullough, Friendswood, TX (US)

( * ) Notice: Subject to any disclaimer, the term of this patent is extended or adjusted under 35 U.S.C. 154(b) by 47 days.

(21) Appl. No.: 16/898,393

(22) Filed: Jun. 10, 2020

(65) Prior Publication Data

US 2020/0383642 A1 Dec. 10, 2020

Related U.S. Application Data

(60) Provisional application No. 62/859,261, filed on Jun. 10, 2019.

(51) Int. Cl.
*A61B 5/145* (2006.01)
*A61B 5/00* (2006.01)
*A61B 5/1473* (2006.01)

(52) U.S. Cl.
CPC ........ *A61B 5/6861* (2013.01); *A61B 5/14507* (2013.01); *A61B 5/14539* (2013.01); *A61B 5/14735* (2013.01); *A61B 5/4866* (2013.01); *A61B 2562/0295* (2013.01)

(58) Field of Classification Search
CPC ......... A61B 5/00; A61B 5/145; A61B 5/1473; A61B 5/14735; A61B 5/6861; A61B 5/14507; A61B 5/4866; A61B 5/14539; A61B 2562/0295; A61B 2010/0061; A61B 10/0045; A61B 1/00156
See application file for complete search history.

(56) References Cited

U.S. PATENT DOCUMENTS

| | | |
|---|---|---|
| 2,773,502 A | 12/1956 | Kaslow |
| 3,118,439 A | 1/1964 | Perrenoud |
| 3,485,235 A | 12/1969 | Felson |
| 3,528,429 A | 9/1970 | Beal |
| 3,683,890 A | 8/1972 | Beal |
| 4,881,952 A | 11/1989 | Masaru |
| 5,738,110 A | 4/1998 | Beal |
| 9,980,634 B2 | 5/2018 | Furuta |

*Primary Examiner* — Eric J Messersmith
(74) *Attorney, Agent, or Firm* — Kearney, McWilliams & Davis, PLLC; William Yarbrough

(57) ABSTRACT

The present invention provides novel approaches to determining the pH level of the upper GI tract, esophagus and stomach, as an indicator of proper GI function, nutrient absorption and as a means to gauge the overall health of a patient down to the cellular level. This may be determined, practically, in real time as a means of testing for and monitoring GI function without need for sedation or invasive procedures.

15 Claims, 4 Drawing Sheets

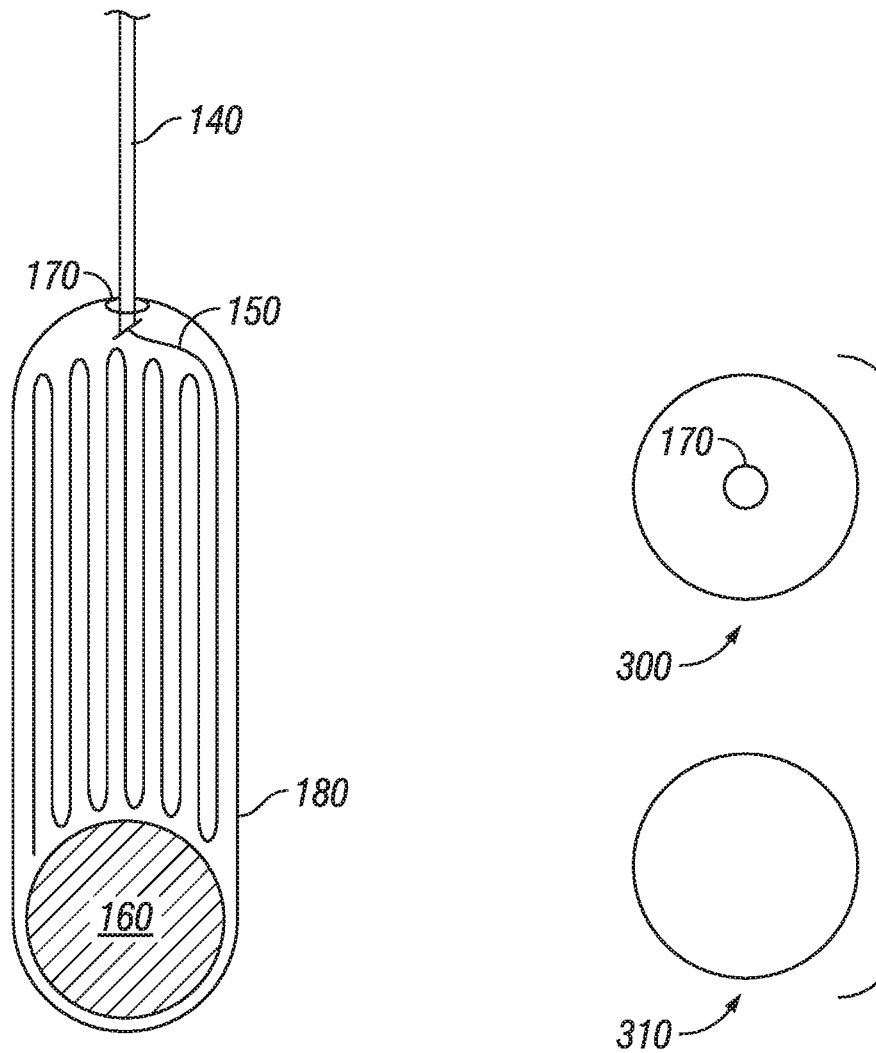

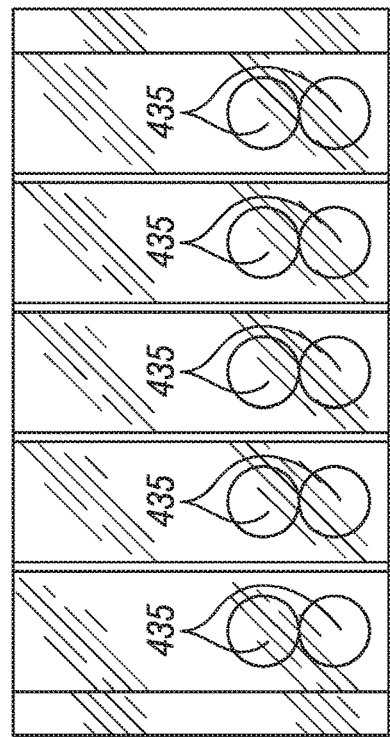
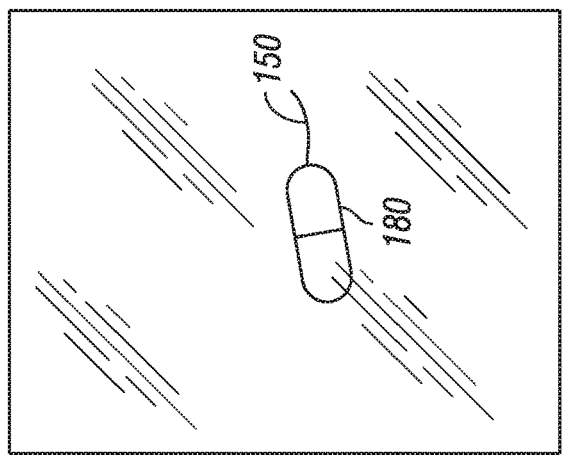
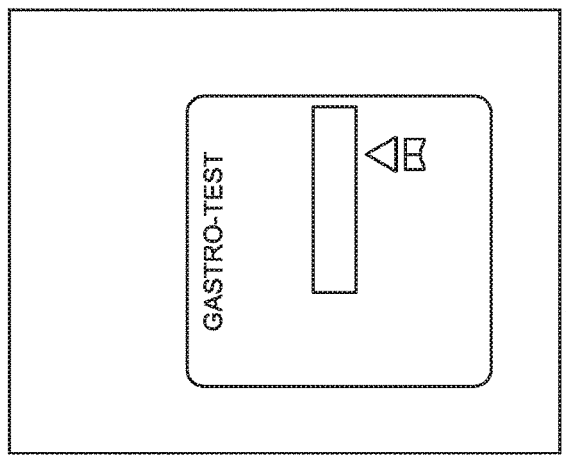
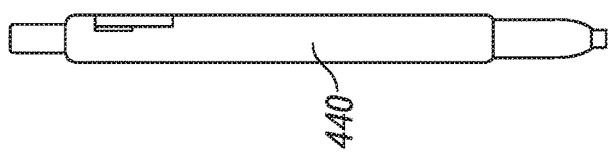
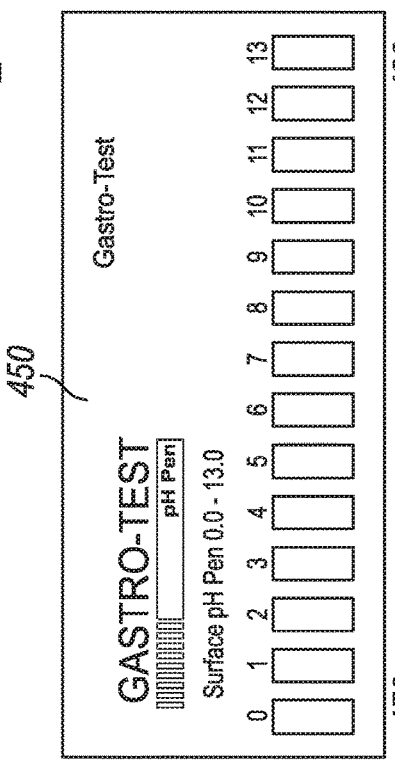
FIG. 4

GASTROENTEROLOGICAL DIAGNOSTIC TEST FOR THE DETERMINATION OF PH IN THE DIGESTIVE TRACT FOR ASSESSMENT OF DYSFUNCTION

CROSS-REFERENCE TO RELATED APPLICATIONS

U.S. Provisional Patent Application No. 62/859,261 filed Jun. 10, 2019

FEDERALLY SPONSORED RESEARCH AND DEVELOPMENT

Not Applicable

INCORPORATION BY REFERENCE

Not Applicable

FIELD OF THE INVENTION

The present invention is a device and method of use utilized to assess, quantify and qualify digestive dysfunction in an individual's alimentary canal, generally, and, specifically, to determine the etiology of symptoms, dysfunction, abnormal physiology and overall health of an individual as it relates to pH in the esophagus and stomach, directly, without gastric intubation or lab-assisted chemical analysis.

BACKGROUND

Historically assessing and determining pH (potential of hydrogen) was used as an indicator to diagnose a particular disease state. In this 'Disease Model', the practitioner is concerned primarily with symptoms that identify disease states whereby a recognized condition or series of conditions are tallied and used to empirically identify a root cause. Once diagnosed, the condition may be treated through any number of remunerative medical protocols, specifically designed for the treatment of that particularized disease or conditions. The disease state is thus defined and categorized by a perceptible symptom or set of symptoms to a known and recognized disorder or dysfunction. This 'disorder' or 'disease state' is then targeted and most commonly corrected surgically, physically (through rehabilitation, life-style changes or similar modifications) or through chemical intervention (i.e. a pharmacological treatment or treatments). If successful, the disease symptoms are either ameliorated or controlled completely with an end goal that symptoms are mitigated and/or disorder or disease is 'cured'.

Yet, this simplistic 'Disease Model' allows for only a narrow view of the operations of the human body and, as such, does not recognize the interdependence of systems, multifactorial causes of signs and symptoms of disease and disorder or, most importantly, the larger picture of the basis of functional and metabolic imbalances of an individual's homeostatic state.

As the field of medical knowledge expands, it becomes more and more apparent that the traditional 'Disease Model' of diagnosis and treatment is insufficient to fully appreciate all of the physical, chemical and physiological mechanisms responsible for maintaining the health of an individual or population. Relying on the simplicity of the 'Disease Model' is comforting in its straightforwardness yet fails to address many systems and facets of those systems that, when understood, allows for a deeper understanding of the origins of system functions, functioning and, most important to the present invention, dysfunction. Simply, rather than coupling a patient's outward manifestations to a particular disease state and treating that specific state, medicine, prospectively must evolve to gain greater comprehension of the antecedent basis of dysfunction that leads to aberrations in a patient's physiology and overall health.

Classically, testing parameters (e.g. temperature, blood sugar, blood pressure, cholesterol, blood work, radiological, fluid collection and weight, etc.) are observed, collected and analyzed to determine their relationship to a specific diseases, condition or illness—where abnormalities are utilized to substantiate an accurate diagnosis. Empirically, this model measures signs and symptoms and equates gathered results to a disease state that is then "treated". By way of example, pH, more specifically abnormal levels of acidity or basicity, are measured and coupled to any number of sequelae (i.e. atrophic gastritis, esophageal bleeding, anemia, thyroid dysfunction or gastric cancers in the form of adenocarcinoma). Yet, this approach to diagnosis is myopic in that treatment is narrowly tailored to a specific condition or state as opposed to remunerative measures that are comprehensive. This model of medicine is reactionary as opposed to preemptive. Signaling a growing paradigm shift, though, medicine is slowly transitioning from a disease model to a physiological dysfunction model involving abnormal cellular environments, externally and internally, resulting in epigenetic modification and a more complete, 'Functional Medicine' approach.

The present device utilizes pH as opposed to a disease diagnosis device wherein abnormal levels of hydrochloric acid assists in assessing dysfunction of normal digestive physiology (i.e. measuring of pH of the stomach reflects a range of normal to abnormal stomach physiology but is not related to a specific disease). Conversely, the present invention may be utilized to confirm normal GI functioning or to 'rule out' causative issues. On a deeper level, stomach pH is related to digestive dysfunction and malabsorption that may consequently result in epigenetic modifications due to changes in the cellular environment of the cell. Manifestly, alterations in pH directly affect the structure and health of every cell in the human body where all growth, repair and functions are related to the digestion of food (pH having a paramount and singular role in digestion and nutrition). So, rather than equating overt symptoms with specific diseases or states, 'Functional Medicine' is concerned with the relationship between the environment in the stomach, its cellular impacts and an individual's overall health state.

Moving from the 'Disease Model' to the 'Functional Model' in medicine, it can be observed that macro variations in pH in the stomach (and resultant digestive irregularities) have a direct effect on micro cellular health of a patient where changes in the extracellular and intracellular composition may cause epigenetic anomalies (in terms of gene expression and protein production) which in turn cause improper cellular genetic regulation and expression up to and including metabolic insufficiencies and dyscrasias. Categorically, the health of the individual is defined by the health of their basic individual components where abnormal cellular environments are outwardly exhibited and are a direct demonstration of exogenous factors such as toxins and endogenous factors such as pH and nutrition.

Succinctly, the stomach is dependent on a precisely maintained (and/or adjusted) acid pH (generally a pH of 1-3) where a closely regulated acidic environment (primarily through hydrochloric acid and histamine) is an absolute requisite for adequate nutritional intake via-a-vis proper digestion. Moreover, the acid of the stomach serves as a bacterial, fungal, viral and parasitic barrier where these non-host challenges, as well as exogenous toxins, may cause untoward imbalances, intoxications and/or disease. Additionally, HCL also acts as a guardian of the immune system of which a substantial portion resides in the intestinal tract. When the stomach is incapable of producing sufficient acid, this results in a two-fold effect where (1) food is not properly broken down and remains undigested (resulting in malnutrition through malabsorption) and (2) bacteria, viruses, parasites and fungi are allowed to survive and proliferate due to an insufficiency of a sufficient HCL barrier and through an abundant access to a putrefied and undigested power source (i.e. residual foodstuffs). Too, exogenous toxins, that would normally be neutralized immediately upon ingestion into the stomach's extremely acidic environment remain active. An overabundance of non-self organisms in combination to the byproducts (i.e. gases) produced from the bacteria, viruses and fungi flow naturally upward, reflux in a retrograde manner through the cardiac sphincter valve and cause damage of both the valve and the esophagus resulting in Gastroesophageal Reflux Disease (GERD), as an end stage resultant, in the Disease Model, but a natural consequence of abnormalities in the pH content of the stomach in the Functional Model.

What is more, food passing into the small intestines, containing undigested food stuff and heightened levels of bacteria, cause dysfunction in the lower part of the alimentary system (e.g. small intestines, large intestines and colon) resulting in inflammation and "leaky gut" or dysbiosis in the small intestines and malabsorption in both the small and large intestines. These undigested and improperly digested foods pass into the bloodstream in an inadequate state for appropriate reduction into usable proteins, fats and fiber which can result in everything from migraine headaches and fibromyalgia to auto-immune conditions and overall poor health. Conversely, excess production of acid can have an equally deleterious effect where the lining of the stomach is detrimentally eroded allowing for conditions such as: cardiac sphincter damage, esophageal erosion, esophageal spasm, pyloric pump dysfunction, ulceration, hiatal hernia, heartburn, regurgitation, dysphagia, pulmonary aspiration and other nutritional abnormalities.

Therefore, physiologic and dysfunction may result in epigenetic modification where gene expression, more pointedly abnormal gene expression, is more a reflection on the internal and external environment of the cell which, when altered, results in transformed genetic expressions (e.g. protein mutations) that are expressed in altered metabolic pathways and physiological and physical manifestations. Where we've come to know "you are what you eat", this should be further modified to say "you are how you digest" as diseases and disease states may be better explained by the relationship of what and how food is digested, how the body processes what is consumed and how that affects cellular functions.

Not surprisingly, when dysfunction is corrected (i.e. "treated"), the "disease" or symptoms of the "disease" are resolved. In actuality, though, no disease existed. The physiological and metabolic dysfunctions are addressed and the body once again is allowed to achieve a homeostatic state and normal anatomy and physiology. The first step to achieving this balance and equilibrium is the accurate assessment of proper stomach and esophageal function (through the determination of acid levels and pH) to ascertain if the major physiologic functional component of digestion, pH, is normal or abnormal as determined through inventor's device.

While strides have been made to overcome the inadequacies of assessing and determining pH as it relates to improper digestion and epigenetic modifications and aberrations, it remains evident that considerable failings remain in the field. It is the goal of the present invention to remedy these shortcomings as to allow better procurement of pH levels that are accurate, non-surgical, practically immediate and minimally invasive. It is another goal of the present device and method of use to potentiate a system of improved understanding of the delicate balance between stomach pH, digestion, nutrition and cell function. It is yet another goal of the present invention to equate subtle variations in pH to specific patient symptoms manifestations where a sliding scale may be used to determine degrees of dysfunction, levels of remunerative intervention and effective prognoses and prevention.

While the inventor has set forth the best mode or modes contemplated of carrying out the invention known to the inventor such to enable a person skilled in the art to practice the present invention, the preferred embodiments are, however, not intended to be limiting, but, on the contrary, are included in a non-limiting sense apt to alterations and modifications within the scope and spirit of the disclosure and appended claims.

SUMMARY OF THE INVENTION

The present disclosure provides a device consisting of a weighted gelatin capsule containing within its enclosure an approximately 50 cm cotton floss (string) composed of highly absorbent, uncoated cotton or like material aligned vertically within said enclosure for ease of release. One end of the floss (string) is made to protrude through an approximately 3 mm orifice in the top of the capsule while the bulk of the floss resides laterally aligned in the interior of the capsule. The protruding floss section is gripped manually or otherwise adhered to the patient and the capsule is swallowed. Through peristalsis and gravity the capsule travels down the esophagus, the string unfurling all the while, until the capsule reaches its terminus whereby the floss completely leaves the capsule. The capsule and the weight, being inert, do not interfere with the functionality of the string and are digested and pass into the stool without consequence. The floss is then removed from the esophagus after a predetermined time (typically 10 minutes), a pH pen is applied to the floss to reveal the pH of the liquid absorbed by the floss (through changing of color corresponding to the pH) and a chart is utilized to match the color (i.e. color corresponding to a specific pH) of the floss to the benchmark of the chart at various lengths corresponding to the floss' location in the alimentary canal (i.e. GI tract). Typically, the length of the floss corresponds to the depth of the organ where the proximal length of the floss is roughly equal to the depth of the esophagus and the distal length (terminus) of the floss is roughly equal to the position of the stomach. The position of the border between the esophagus and stomach (i.e. the cardiac sphincter) can be approximated with great accuracy by determining the length of the string and by color changes upon the string.

Also, the present invention may be used to successively test the pH of a patient where a base line may be followed by a post-challenge test. In this case, a normal (fasting) state may be analyzed to determine the 'resting' pH, at time zero, and then challenged by an HCL inducing substance (e.g.

caffeine tablets), at time 1, 2, 3 etcetera to determine (1) the patient's ability to mount a response to a challenge and (2) the time that that response takes to occur. Successive testing can occur within one visit, to make contemporaneous determinations by way of comparison, across several visits to monitor functionality or a combination thereof.

Advantages of the above invention and method of use include a safe, non-invasive, non-incisive, non-pharmaceutical, non-surgical pH determining tool that offers immediate results (less than or equal to 10 minutes), can be conducted consecutively, has in-office applicability, non-laboratory (requiring no pathological assessment) interpretation that is inexpensive, portable, easy to use exhibiting a potentially vastly extended shelf life.

Specifically, the system of analysis and resulting pH values of the present invention provides are as listed below:

Fasting: pH 1-2=hyperacidity, low pH, hyperchlorhydria
1-3=normal fasting
4-8=hypoacidity, high pH, hypochlorhydria
After challenge with caffeine if original test is >4
1-3=normal acidity
4-6 mild hypochlorhydria, high pH low functional stomach acid
>6=severe hypochlorhydria, high pH, very low functional stomach acid Any pH <6 on the distal string or proximal to the mouth is indicative of acid reflux though the cardiac sphincter into the esophagus.

Additional advantages of the present invention include (1) an uncoated string whereby chemical decomposition does not occur over time (increasing storage life), (2) no chemical reaction distorts results, (3) uncoated string promotes absorption of fluids, (4) different areas of the GI tract are accessible with one tool (along the length of the string) during a single test or across multiple tests, comparatively, and (5) multiple tests may be used for baseline and challenged results sequent during a single visit or over several follow-up visits.

Another advantage includes the ability of the practitioner to access the "health" of the "Stomach Acid Barrier" by determining if the patient has a resting stomach acid capable of functioning properly as a defense against bacteria, viruses, parasites and other pathogens, as well as other non-self and exogenous toxins, that can adversely affect the body and/or a patient at greater risk for disease. Furthermore, the present device can test and measure if a patient has the ability to quickly summon an appropriate immunological response in reply to a non-self stimuli thus addressing functionality and possible dysfunction.

Yet another advantage is the lateral placement of string and the ergonomic uncoiling upon deployment wherein the noninterfering state of both the capsule (harboring the uncoiled string but being otherwise unattached) and stainless-steel ball (proving frictionless, inert surface while in proximity with the string) promote unfettered unfolding, free release and inert interaction with the string.

While medicine has for centuries been disease-focused, it is paramount that a paradigm shift occurs in determining and developing a forward-looking proper functioning of cells, organs and systems analysis over a reactionary signs and symptoms-based strategy for observing and maintaining health. And while strides have been made to overcome unaddressed inadequacies in the field, much remains to be accomplished in remedying past and present failings. It is the goal of the present invention to remedy the infirmed ability of 'Disease Model' to speak to shortcomings, systemic infirmities and antiquated institutional approaches as to allow better analysis, diagnosis and monitoring of proper and improper functioning within the body. It is toward this end that inventor presents the novel, currently improved invention and method of use as to potentiate efforts in this area.

While inventor has set forth the best mode or modes contemplated of carrying out the invention known to inventor such to enable a person skilled in the art to practice the present invention, the preferred embodiments are, however, not intended to be limiting, but, on the contrary, are included in a non-limiting sense apt to alterations and modifications within the scope and spirit of the disclosure and appended claims.

DESCRIPTION OF PREFERRED EMBODIMENTS

Advantages of the present invention will become readily apparent to those skilled in the art from the above Summary and following Detailed Description, wherein there is described certain preferred embodiments of the invention, and examples for illustrative purposes. Although the following detailed description contains many specific details for the purposes of illustration, one of ordinary skill in the art will appreciate that many variations and alterations to the following details are within the scope of the invention. Accordingly, the following embodiments of the invention are set forth without any loss of generality to, and without imposing limitations upon, the claimed invention. While embodiments are described in connection with the description herein, there is no intent to limit the scope to the embodiments disclosed herein. On the contrary, the intent is to cover all alternatives, modifications, and equivalents According to one preferred embodiment, the present invention provides a non-surgical, non-invasive, highly accurate means of determining the pH of the esophagus and stomach that has no long-lasting side effects, requires no pharmaceutical intervention (e.g. sedatives), is inexpensive, fast, mobile, ambulatory, requires no specialized equipment or facilities, necessitates minimal training and is available as an (FDA Class 1 exempt) diagnostic device.

In one preferred embodiment of the present invention the gelatin capsule is a 00 vegetable/gelatin capsule, the floss string is an approximately 50 cm, highly absorbent, non-coated cotton string, and the weighted (distal) portion of the capsule is weighted by a 3/16 stainless steel ball bearing or other like weight bearing material.

According to another preferred embodiment, the methods of collecting information involves a reusable pH pen and color pH chart for the determination of pH of the esophagus and stomach that may have an accompanying manual for proper device use, implementation, reading and recording.

In a preferred embodiment of the present invention, the present device measures various levels of acidity and basicity (i.e. pH level) as opposed to a binomial presence or absence of acid (achlorhydria) where a non-impregnated, chemical free floss is positioned within the capsule vertically (as opposed to coiled about the capsule interior or horizontally) to facilitate better release.

In another preferred embodiment of the present invention, the capsule is weighted with a steel bearing or other like weight that is designed to travel down the digestive tract (within said gelatin capsule) and release fully, allowing the capsule to be passed down the lower half of the GI tract (small intestine, large intestine and colon), dissolved in the GI tract, or a combination thereof, for final release through excretion.

The present invention also encompasses a device wherein the pH pen and pH chart are reusable and may accompany several pH determining floss filled capsules. Conversely, the pens may be one time use pens.

The present invention may further encompass a means to determine the initial and subsequent steps in the digestive process (via the assessment of the functioning of the esophagus and stomach) in combination with a guaiac test to test for occult blood in the stool. Yet, the device can be used to further gauge many varied operations of the digestive system including: the function of both pyloric and cardiac sphincter functions, the presence or absence of reflex, the level of nutrients (protein and fat) breakdown, calcium absorption (where calcium serves as an indicator of potential for osteoporosis), stomach tissue health, dysbiosis (i.e. leaky gut), vagus nerve function, purification prediction, T4-T6 segmental dysfunction, motility issues, abdominal pain and spasm origins and general vitamin and mineral deficiencies.

In yet another embodiment, the present invention and method of use may be used to screen for physiological dysfunction including esophageal spasm, pyloric pump dysfunction, pulmonary aspiration, dysphagia, secretion obstructions, or a combination thereof.

In another embodiment, the present invention and method of use may be used as a preventative diagnostic tool in which the present device may be used to omit suspected causes of digestive dysfunction and/or confirm suspected dysfunction.

In yet another embodiment, the present invention and method of use may be utilized to monitor the effectiveness of treatment or the temporal progression or regression of abnormal digestive function currently undergoing treatment.

BRIEF DESCRIPTION OF THE DRAWINGS

While the novel features and method of use of the application are set forth above, the application itself, as well as a preferred mode and method of use, and advantages thereof, will best be understood by referencing to the following detailed description when read in conjunction with the accompanying drawings in view of the appended claims, wherein:

FIG. 2 illustrates a weighted capsule with vertically oriented cotton string.

FIG. 3 depicts a top and bottom view of the present invention.

FIG. 4 is a complete testing kit with the present invention and diagnostic tools.

DETAILED DESCRIPTION

A detailed description of the preferred embodiments of the invention is disclosed and described below. Yet, each and every possible permutation, within the limits of the specification, are not disclosed as various variations are postulated to be in the purview and contemplation of inventor and those having skill in the art. It is therefore possible for inventor and those having skill in the art to practice the disclosed invention while observing that certain placements and spatial arrangements are relative and capable of being arranged and rearranged at various points about the invention that nonetheless accomplishes the stated goals, advantages and/or correction of one or more of the infirmities outlined and discussed above.

Equally, it should be observed that the present invention can be understood, in terms of both design and function, from the accompanying disclosure and claims taken with reference to the associated drawings. And whereas the present invention and method of use are capable of several different embodiments, which can be arranged and rearranged into several configurations, such may be accomplished without departing from the scope and spirit of the present application as shown, described and presented herein.

Figure 1:
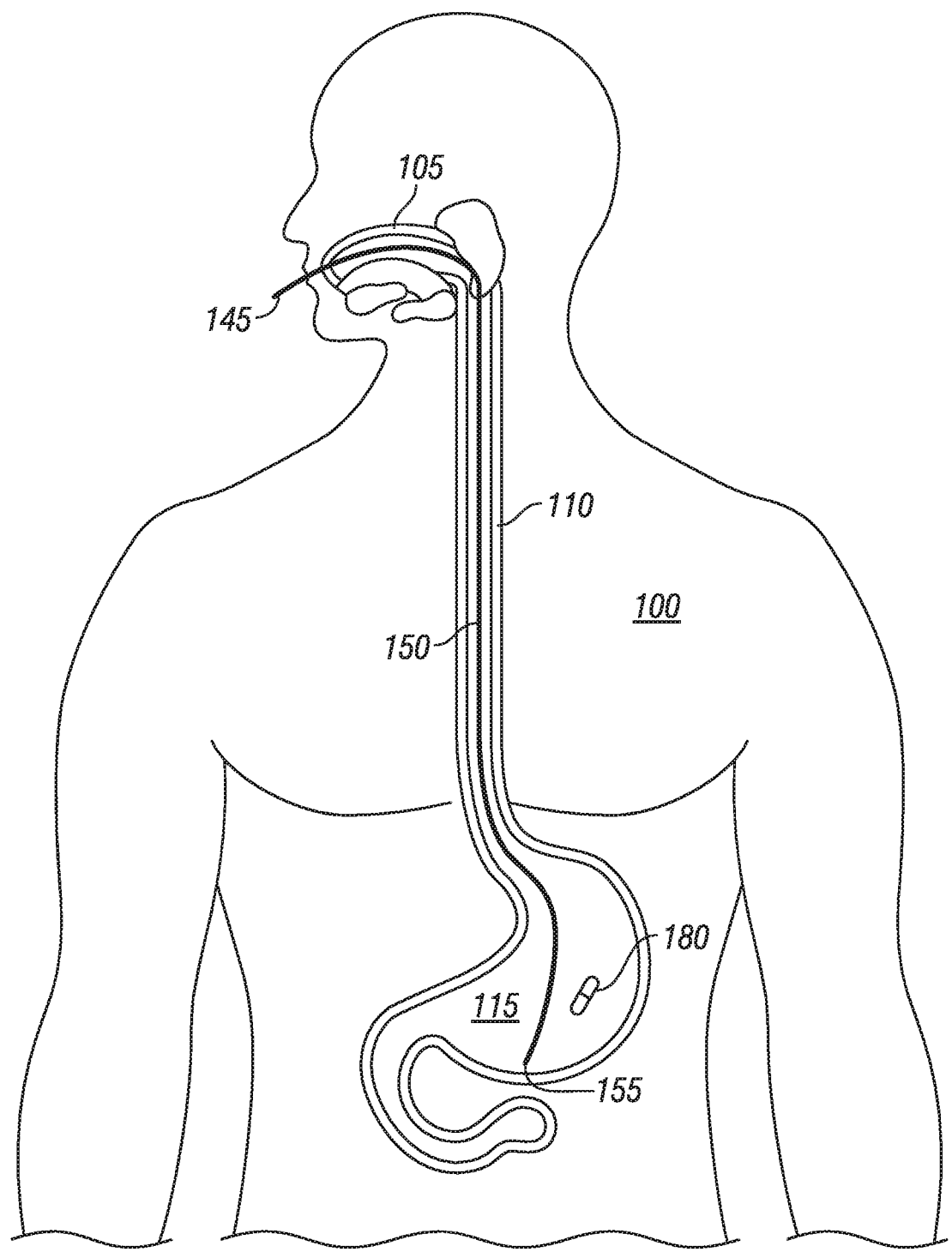
FIG. 1 is a depiction of a patient having ingested the present invention.

As depicted in FIG. 1, upon ingestion into the gastrointestinal (GI) tract of patient 100, the capsule 180 traverses the buccal cavity and mouth 105, travelling down the esophagus 110, aided by peristalsis and gravity, until finally coming to rest in the stomach 115. It should be noted that cotton string 150, has become unfurled and released from capsule 180 thereby allowing capsule 180 to pass through the remainder of the GI tract, dissolved or partially dissolved, without incident to be excreted. In terms of placement, it may be observed that proximal string end 145 resides outside of patient 100 and distal string end 155 resides within the lumen of the stomach 115.

FIG. 2 provides a detailed, interior view of capsule 180 which is preferable an '00' sized vegetable or gelatin capsule (while capsule sizes capable of greater and lesser capacity are within the contemplation of inventors). The capsule 180 itself exhibits a 3 mm uniport 170 (see also FIG. 3 capsule top 300) evidenced as an aperture at the apex and point of cotton string 150 for string exodus as the capsule 180 descends down and through the alimentary canal. Further cotton string 150 is typically 50 cm in length, but may be adjusted (lengthened or shortened) as to accommodate a specific patient or a patient's age, and may consist of a uniformly thick string, yarn or cloth (as depicted in FIG. 1) or may evidence a leader 140 that is of a greater or lesser thickness as to accommodate grip or ease of adhesion to a patients exterior cheek or face. Of note, the preferred cotton string 150 is 100% cotton, but may be of a cotton or similar material or blend of materials that allows for gastric and esophageal liquid absorption sufficient to allow for retrieval of a quantity adequate for pH testing and pH determination, which is conspicuously uncoated (again allowing for proper liquid absorption) and unconnected to capsule 180 or stainless steel ball 160 as to allow for a complete removal of cotton string 150 from capsule 180 and capsule 180 release into the lower GI tract for eventual expulsion. Too, capsule 180 can be seen to manifest a stainless-steel ball 160 within the capsule 180 at its interior, distal end to facilitate movement down and into the stomach of the capsule 180 through the dual effects of gravity and peristalsis. Of special attention, is the capability of both the capsule 180 and stainless-steel ball 160 to facilitate and ferry cotton string, through deployment and into designated lumens, without (1) chemically interacting with or (2) otherwise encumbering advancement to its terminus.

As additionally provided in FIG. 3 capsule 180 and uniport 170 can be viewed from a superior view 300 of capsule 180 whereas the inferior view 310 exhibits no such opening.

FIG. 4 illustrates a complete kit whereby the following is provided: a sealed, sterile gastro-test packet (front view 410 and rear view 420), a pH pen 440, a pH card 'Universal Indicator' 450 and a plurality of caffeine tablets 435 by which to accomplish a challenge test for pH production within the stomach 115.

Testing Device

The device that is the present invention, as illustrated in 420 as capsule 180 and uniformly sized cotton string 150, is the functional and operational component of the invention intended for ingestion by a patient. Typically, this capsule 180 is ingested and the distal portion of the cotton string 145 is either held or taped to the patient's exterior cheek. It may be advisable to administer capsule 180, and accompanying cotton string 150, with the head tilted back and may be administered with water, prior to and with ingestion. A natural 'gag' reflex may be observed by the administrator and experienced by the patient, which is natural and to be expected. Given one to several minutes, this sensation should subside, and patient should be better able to tolerate feeling a sense of nausea. Once ingested, the capsule will travel down the esophagus 110 and the string will exit the uniport 170 in capsule 180 until reaching its most distal portion 155 which, upon leaving the capsule 180, will reside in the stomach 115 lumen. Capsule 180, and dissolved or partially dissolved components thereof, will continue to move through the GI tract (through both the small and large intestines, past the colon and exiting the body), and may completely or partially dissolve and dissipate. This will result in the final passing of, most probably, the components of capsule 180 and accompanying non-dissolvable stainless-steel ball 160

Ideally, once ingestion has occurred, and the string 150 is fully deployed, the patient should be instructed to minimally lie on patient's left side for 2 minutes, back for 2 minutes and right side for 2 minutes where a total residency time for the ingested string is preferably an average of 10 minutes before removal of the string 150 to allow for proper liquid absorption and string 150 saturation.

Once the cotton string 150 has fully deployed and achieved a residency time sufficient for gastric (stomach) 115 and esophageal 110 liquid absorption and saturation, the cotton string 150 is then manually removed from the patient 100 and 'marked' with a pH pen 440 acting as a pH indictor as to determine hydronium ions (H3O+) or hydrogen ions (H+). The pH pen 440 then reveals the pH of approximately the areas of the mouth 105, the esophagus 110 and the stomach 115 through demarcations derived through observance of the color changes. Additionally, the colors themselves reveals the pH of each area.

pH Indicator Pen

The pH indicator pen contains chemically reactive substances in the form of halochromic material that provide a color change indicator corresponding the pH responsible for induced color change on the cotton string 150. In general, the materials exhibited by the pH indicator pen 440 should react with equal sensitivity to acids and bases, practically altering the wavelength of absorbed light in each case reflected to an observers eye, and resulting in a color change corresponding to the relative amount of hydrogen and hydroxide, respectfully. For example, an acidic liquid, here stomach acid in the range of 1-3, should be represented by a high concentration of hydrogen ions and the display of a dark red to red color. Alternatively, a basic liquid, displaying a larger concentration of hydroxide ions in the range of 7-11, would display a green to blue color.

pH Card Universal Indicator

The kit of FIG. 4 includes a 'Universal Indicator' 450 whereby certain pH values are exhibited as a range of values, measured on a logarithmic scale, indicating acidity or alkalinity of a particular solution and, in this case, gastric and esophageal liquids. Once removed from the patient's GI tract, the halochromic material of the pH indicator pen 440 is immediately applied to the cotton string 150 designating (1) demarcations between anatomical structures (i.e. color change from a string area corresponding to a patient's stomach to a color change correlated with the area of the esophagus) and (2) relative acid exhibited in these structures (e.g. darker red indicating a stronger acidity and orange to yellow indicating weaker acids).

The lower the value of the scale, moving left of neutral 7 at 470, hydrogen ion activity is greater, and more acidic, whereas moving right of neutral 7 at 480, the hydroxide ion activity is greater and more basic. In general strong acidity, where pH is in the range of 1-3, would be evidenced as red, weak acidity, pH in the 3-6 range, evidences as orange to yellow, neutral, pH 7, is green, weak alkali, pH 8-11, is blue and strong alkali, pH 11 and above, is violet to indigo.

Figure 5:
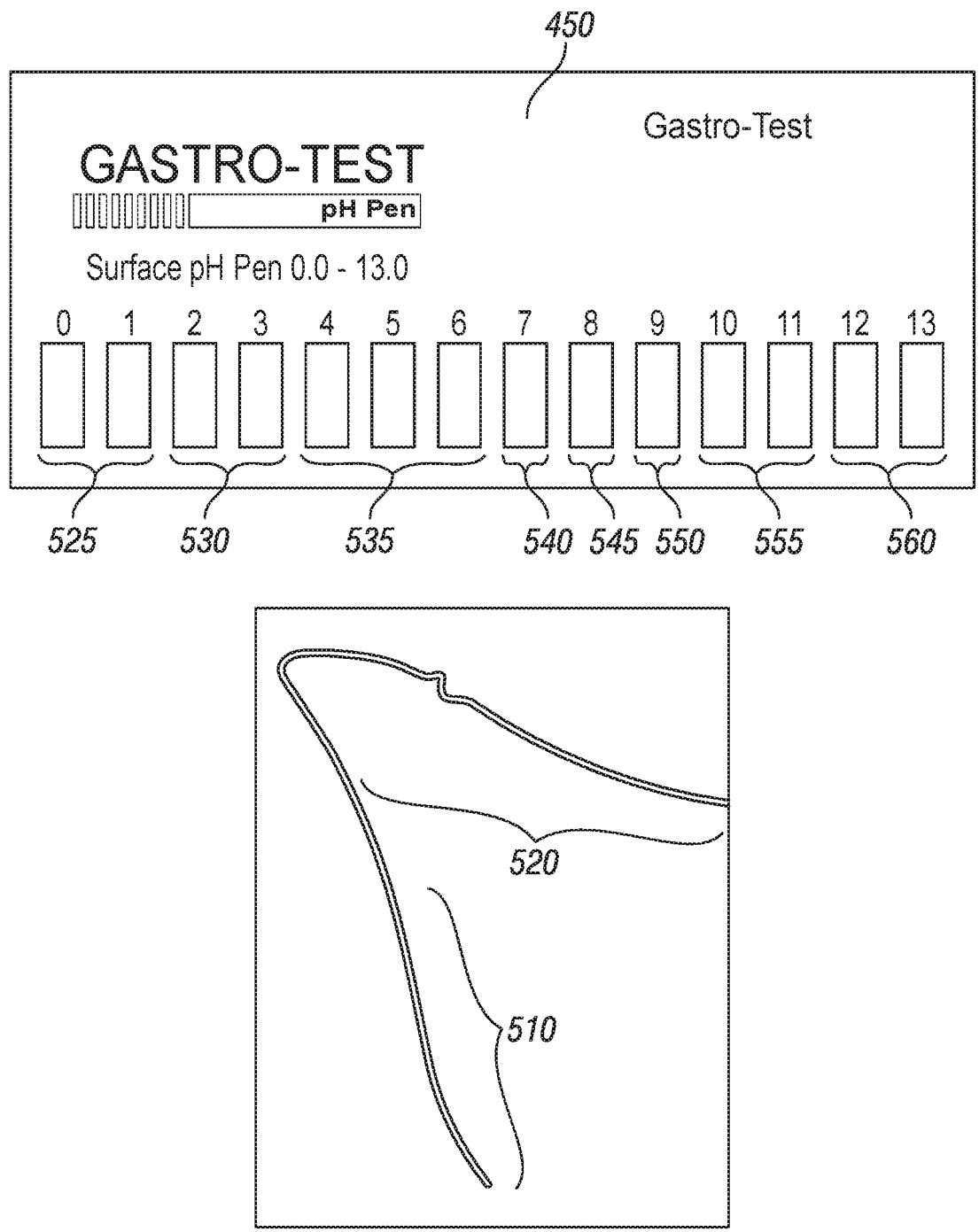
FIG. 5 represents a completed diagnostic test.

By way of example, FIG. 5 displays the results of a typical diagnostic use of the present invention whereby the area designated as 510 may display an area of color change designating the point at which the esophagus terminates and the stomach begins at a point commonly referred to as the gastroesophageal sphincter or cardiac sphincter, at the proximal portion of 510, and the area designated as 520 can be postulated to correspond to cotton string's placement in the esophagus. What is more, the richness or lightness of a color can, in addition to delimitations of anatomical structures, aid in determining the amount of acidity or alkalinity. Determinations as to the juncture between the mouth/buccal cavity can as well be determined at the point constituting the pharynx.

Expressly, where referencing 'Universal Indicator' 450 has regions as follows:

Area 525: '0' is signified by a dark, wine red, '1' is represented by a tomato red;

Area 530: '2' is a rust orange and '3' is an orange red (marigold);

Area 535: '4' is represented by a gold yellow, '5' amber yellow to honey yellow '6';

Area 540: '7' is a true yellow;

Area 545: '8' is a green to blue green;

Areas 550: '9' is a cerulean;

Area 555: "10 is an eggplant and '11' is a cobalt blue;

Area 560; '12' is a royal blue and '13' is a dark violet/indigo blue.

Therefore, if the color ranges of the cotton string 150 depicted in FIG. 5 at 510 were darker red, '0' to '1' 525 results on the 'Universal pH Indicator' chart 450, this would indicate a more acidic environment (possibly indicating rebound acid hypersecretion, Zollinger-Ellison syndrome, gastric outlet obstruction, H. pylori and the like) and an orange-red, '2' to '3' 530 or a yellow-orange 535 could indicate a less acidic environment in the stomach (e.g. potential achlorhydria) as an underlying cause. As well, an orange red '2' to '3' 530 or even '0' to '1' 525 in the esophagus could implicate gastric reflex (potentially caused by diet, lifestyle or anatomical deficiencies). Specifically, and most importantly these results can be obtained through a minimally invasive, easily repeatable means of not only quickly and efficiently determining the state of the patient in real time but also allow a practitioner to 'spot check' and monitor a patient practically instantly without need for sedation or invasive diagnostic procedures (unless further warranted).

Too, the ability of a patient's body to rapidly increase HCL levels may be determined with the use of caffeine tablets 435 whereby HCl production may be stimulated with the introduction of caffeine prior to administration of a test or after an initial test has been administered. This allows a practitioner to measure a base HCL production, after fasting, and under HCL production enhancing conditions in response to a stimuli (in a challenged state with caffeine tablets 435). This two-step testing procedure allows the practitioner to gain two sets of results for both a resting and challenged state and the ability to assess the body's ability to function normally and the detect abnormal function—both functional conditions that are not necessarily tied to a particular disease state.

The present invention evidences many advantages over the prior art including at least the following: (1) a lack of chemical or coating on the ingested string (thus enhancing absorption and pH display), (2) an accurate means of determining the stomach acid barrier evidenced by a patient as a means to effectively neutralize and manage bacteria, viruses, parasites, allergens and other foreign material ingested by a patient, (3) a unique folding of a diagnostic string—avoiding untoward tangling, (4) an unattached capsule and sterling-steel ball that remain unattached and provide only a vehicle for proper string placement in an inert (non-reactive) vehicle and (5) a means to test and retest in close succession for resting and challenged states that is (6) minimally invasive and infinitely repeatable.

The particular embodiments disclosed are merely illustrative, which may be apparent to those having skill in the art that may be modified in diverse but equivalent manners. It is therefore contemplated that these particular embodiments may be altered and modified and that all such alterations are considered within the scope and spirit of the present application. And while these illustrations are of a limited number set, it is clear that the invention itself is mutable to any number of arrangements, configurations and modifications without departing from the invention's spirit thereof.

I claim:

1. An ingestible device and metabolic dysfunction assessment tool for determining the pH level of the upper GI tract, esophagus and stomach, as an indicator of proper GI function, nutrient absorption and as a means to gauge the overall health of a patient comprising:
   an uncoated, fluid absorbing string;
   said string residing almost entirely within a capsule, made to exhibit a partial, protruding end outside of said capsule for manual grasping wherein said string resides within said capsule interior laterally;
   said capsule exhibiting a uniport at least one capsule apex for string egress;
   said capsule designed to transport an unfurled portion of said string through the esophagus into the stomach;
   said string made to unfurl while traveling through the upper GI tract due to the combined effects of peristalsis and gravity;
   said capsule made to remain otherwise unattached to said string;
   a weighted sphere within said capsule residing in the lower third of said capsule;
   said weighted sphere made to remain otherwise unattached to said string;
   said string made to completely unfurl upon descent through the GI tract, a section of the string coming to rest in the stomach;
   said string made to be allowed to rest in the esophagus and stomach for a length of time sufficient to allow for adequate string saturation with esophagus and stomach liquid; and
   wherein said capsule, dissolved or partially dissolved, and said weighted sphere are made to pass to excretion.

2. The device of claim 1 wherein said string is cotton or a cotton blend that is sufficiently absorbent to allow for saturation with esophagus and stomach fluid.

3. The device of claim 1, wherein said partial, protruding end outside of said capsule for manual grasping is made to be alternatively adhered to the outer cheek of a patient.

4. The device of claim 1, wherein, after resting in the esophagus and stomach for a length of time sufficient to allow for adequate string saturation with esophagus and stomach liquid, said string is made to be removed from patient.

5. The device of claim 4 wherein the resting time is approximately 10 minutes.

6. The device of claim 2, wherein, the gripped partial, protruding end is made to be utilized to remove said device from patient's GI tract.

7. The device of claim 5 wherein, after removal from the patient, said string is made to accept application of a pH indicator pen containing a chemically reactive substance in the form of halochromic material that provides a color change indication corresponding to a particular pH exhibited on said cotton string.

8. The device of claim 7, wherein said string is made to allow a pH Universal Indicator to assess a pH of at least one portion of said string after said string is made to accept application of a pH indicator pen and said color change is indicated.

9. The device of claim 8 wherein the color change on said at least one portion of said string made to accept said application of said indicator pen is used to (1) determine an area corresponding to an anatomical feature giving rise to said fluid and (2) determine a pH within said anatomical feature.

10. A method for determining the metabolic function of a patient by determining the pH level of the upper GI tract, esophagus and stomach, as an indicator of proper GI function, nutrient absorption and as a means to gauge the overall health of a patient by introducing the device of claim 1 into the alimentary tract of a patient;
   introducing the capsule of said device into a patient's mouth for ingestion;
   gripping, or otherwise adhering to patient's cheek, the exposed string portion of said string;
   allowing said string to unfurl from a lateral orientation of said string and from said capsule through an aperture in said capsule as said capsule descends through the esophagus and into said stomach due to peristalsis and gravity;
   allowing said string to completely disengage from the capsule and the weighted sphere;
   allowing said string to remain within a patient's esophagus and stomach for a sufficient time to become saturated with esophagus and stomach liquids;
   removing said string;
   coating said string with a content of a pH indicator pen containing a chemically reactive substance in the form of halochromic material; observing color changes due to different pH content of each liquid;
   comparing those colors to a universal pH indicator card; and determining, from string color change, and indicator card designation, (1) demarcation of boundaries of anatomical structures and (2) pH within those structures.

11. The method of claim 10 wherein said anatomical structures include, but are limited to, a patient's mouth, a patient's buccal cavity, a patient's pharynx, a patient's esophagus, a patient's cardiac sphincter, a patient's stomach or a combination thereof.

12. The method of claim 10 wherein pH is utilized to determine the acidity of the mouth, pharynx, esophagus, stomach, or a combination thereof, in order to assess proper functioning of each anatomical feature, singularly, and in combination.

13. The method of claim 12 wherein said pH determination may be administered sequentially, at the same visit with an administrator, fasting, after challenge, consecutively over time, or a combination thereof as to assess the functionality of said anatomical features.

14. The method of claim 12 wherein said pH determination is used to assess proper HCl production, over production of HCL, under production of HCL, dysbiosis, proper stomach functioning, proper esophagus functioning, proper digestion, chemical functionality of the stomach, measurement of the "Stomach Acid Barrier", a two-step resting and challenge induced acid production capability, underlying disease or disorder of the stomach or esophagus, or a combination thereof.

15. The method of claim 12 wherein said method is used to assess, diagnose, challenge and monitor features of the GI tract in terms of function and dysfunction.

* * * * *